(12) United States Patent
Banov (10) Patent No.: US 9,173,940 B1
(45) Date of Patent: Nov. 3, 2015

(54) MIXTURE OF BETAMETHASONE AND TRANILAST WITH A TRANSDERMAL GEL FOR SCAR TREATMENT

(71) Applicant: Daniel Banov, Sugar Land, TX (US)

(72) Inventor: Daniel Banov, Sugar Land, TX (US)

(73) Assignee: PROFESSIONAL COMPOUNDING CENTERS OF AMERICA (PCCA), Houston, TX (US)

( * ) Notice: Subject to any disclaimer, the term of this patent is extended or adjusted under 35 U.S.C. 154(b) by 0 days.

(21) Appl. No.: 14/265,098

(22) Filed: Apr. 29, 2014

(51) Int. Cl.

| | | |
|---|---|---|
| *A61K 38/47* | (2006.01) | |
| *A61K 47/12* | (2006.01) | |
| *A61K 31/573* | (2006.01) | |
| *A61K 31/196* | (2006.01) | |
| *A61K 38/48* | (2006.01) | |
| *A61K 36/48* | (2006.01) | |
| *A61K 47/14* | (2006.01) | |
| *A61K 47/10* | (2006.01) | |
| *A61K 47/20* | (2006.01) | |
| *A61K 47/24* | (2006.01) | |
| *A61K 47/34* | (2006.01) | |
| *A61K 9/06* | (2006.01) | |

(52) U.S. Cl.
CPC . *A61K 47/12* (2013.01); *A61K 9/06* (2013.01); *A61K 31/196* (2013.01); *A61K 31/573* (2013.01); *A61K 36/48* (2013.01); *A61K 38/47* (2013.01); *A61K 38/4886* (2013.01); *A61K 47/10* (2013.01); *A61K 47/14* (2013.01); *A61K 47/20* (2013.01); *A61K 47/24* (2013.01); *A61K 47/34* (2013.01); *C12Y 302/01035* (2013.01)

(58) Field of Classification Search
None
See application file for complete search history.

(56) References Cited

U.S. PATENT DOCUMENTS

| | | | | |
|---|---|---|---|---|
| 2010/0278784 A1* | 11/2010 | Pojasek | ........... | A61K 8/498 424/93.7 |
| 2014/0348873 A1* | 11/2014 | Banov | ........... | A61K 8/898 424/195.17 |
| 2014/0350106 A1* | 11/2014 | Banov | ........... | A61K 31/17 514/559 |
| 2014/0371322 A1* | 12/2014 | Glasnapp | ........... | A61K 31/138 514/652 |

OTHER PUBLICATIONS

PCCA PracaSil-Plus fact page from www.pccarx.com.au.*
Banov D. et al. Case Series: The Effectiveness of Fatty Acids from Pracaxi Oil . . . Dermatology and Therapy 4(2)259-269, Dec. 21014.*
Saeki H. et al. Guidelines for Management of Atopic Dermatitis. J of Dermatology 36(10)563-577, Oct. 2009.*
PCCA PracaSill-Plus factpage from www.pccarx.com.au 2012.*
Banov D. et al. Case Series: The Effectiveness of Fatty Acids from Pracaxi Oil . . . Dermatologyand Therapy 4(2)259-269.*
Saeki H. et al. Guidelines for Managementof Atopic Dermatitis. J of Dermatology 36(10)563-577, Oct. 2009.*

* cited by examiner

*Primary Examiner* — Ralph Gitomer
(74) *Attorney, Agent, or Firm* — Barnes & Thornburg LLP; Thomas J. McWilliams; Edward F. Behm, Jr.

(57) ABSTRACT

The present disclosure relates to a synergistic mixture of betamethasone valerate and tranilast combined with a transdermal gel using skin permeation enhancement for application in scars for reducing or preventing the abnormal scar formation, specially keloids and hypertrophic scars. The disclosed synergistic mixture may exhibit permeation enhancing properties. The transdermal gel may include a mixture of silicone, phosphatidylcholine, pracaxi oil, and seje oil; one or more oils having essential fatty acids, behenic acid, oleic acid; one or more skin lipids; a butter having linoleic acid and linolenic acid; and solvents as transdermal penetration enhancers.

20 Claims, 4 Drawing Sheets

MIXTURE OF BETAMETHASONE AND TRANILAST WITH A TRANSDERMAL GEL FOR SCAR TREATMENT

CROSS REFERENCE TO RELATED APPLICATIONS

N/A

BACKGROUND

1. Field of the Disclosure

The present disclosure relates in general to pharmaceutical treatments, and more particularly, to permeable enhanced compositions to treat scars.

2. Background Information

Cuts, wounds, and surgical incisions are repaired due to the skin's constant ability to shed old cells and create new ones. Nevertheless, this process also results in the production of scars. While a visible scar may be the necessary and inevitable end to the healing process, the results vary with the individual. Some visible scars fade and improve in appearance, while others provide evidence of injury for decades to come. A physical injury to the body causes disruption in body structure. The wound may be present only under the skin, may affect only the skin surface, or may involve both.

Transdermal treatments have received increased attention. One limitation of the use of medication, such as Tranilast, in topical treatments is the permeability and its ability to reach the target area, passing through the stratum corneum which is responsible for providing a protective barrier against environmental damage, as the outermost layer of the epidermis consisting principally of dead epithelial cells that are filled with the protein keratin that waterproofs and toughens the skin. This characteristic of the skin may provide a difficulty for topical treatment to permeate through the skin in order to get to the inner layers of the skin, causing active pharmaceutical ingredients (API) not being easily permeated through the skin when employed in cosmetic products or pharmaceutical formulations that are topically or transdermally delivered.

There is still a need for transdermal formulations which include permeation enhancers that may increase skin permeability of API to reduce the abnormal scar formation in a short period of time, specially hypertrophic scars and keloids.

SUMMARY

An aspect of the current disclosure is a formulation, which includes a synergistic mixture of betamethasone valerate and tranilast with a transdermal gel, for suppressing collagen synthesis for keloids and hypertrophic scars. Formation of an hypertrophic scar or keloid may be prevented by applying pharmaceutically effective amount of synergistic mixture of betamethasone and tranilast with a transdermal gel, capable of inhibiting expression of collagen and, therefore, reducing abnormal scars.

In an embodiment, the disclosed formulation may include a synergistic combination of about 0.05% w/w to about 1% w/w of betamethasone valerate; about 0.2% w/w to about 5% w/w of Tranilast; and about 50% w/w of a transdermal gel. The transdermal gel may include about 0.5% w/w to about 10% w/w of pracaxi oil, being most suitable about 0.5% w/w to about 5% w/w; about 0.5% w/w to about 10% w/w of seje oil, being most suitable about 0.5% w/w to about 5% w/w; about 0.1% w/w to about 5% w/w of phosphatidylcholine, and about 10% w/w to about 95% w/w of silicone.

According to other embodiments, the transdermal gel may include one or more oils having essential fatty acids, such as behenic acid and oleic acid; one or more skin lipids; and a butter having linoleic acid and linolenic acid.

In other embodiments, transdermal gel may include organic solvents as transdermal penetration enhancers, such as caprylic/capric triglycerides (medium chain triglycerides), ethyl alcohol, ethoxy diglycol, dimethyl sulfoxide (DMSO), glycerin, isopropyl myristate, isopropyl palmitate, and propylene glycol, among others.

According to an embodiment, disclosed formulation may be transdermally administered directly into a scar, twice a day (between about 2 g to about 6 g) during about 12 weeks to about 20 weeks, expecting results to show from the second week to a month after starting administration.

Numerous other aspects, features of the present disclosure may be made apparent from the following detailed description, taken together with the drawing figures.

BRIEF DESCRIPTION OF THE DRAWINGS

The present disclosure can be better understood by referring to the following figures. The components in the figures are not necessarily to scale, emphasis instead being placed upon illustrating the principles of the disclosure. In the figures, reference numerals designate corresponding parts throughout the different views.

FIG. 1 illustrates the scar images of two test group volunteers (A and B).

FIG. 2 depicts the skin contour replicas of two test group volunteers (A and B).

FIG. 3 shows the overall appearance of the patient's new scar before and two weeks after the application of the transdermal gel.

FIG. 4 shows patient's facial scars before and after the application of the transdermal gel.

DETAILED DESCRIPTION

The present disclosure is here described in detail with reference to embodiments illustrated in the drawings, which form a part here. Other embodiments may be used and/or other changes may be made without departing from the spirit or scope of the present disclosure. The illustrative embodiments described in the detailed description are not meant to be limiting of the subject matter presented here.

DEFINITIONS

As used here, the following terms may have the following definitions:

"Gel" refers to a colloid in which the solid disperse phase forms a network in combination with that of the fluid continuous phase, resulting in a viscous semi-rigid solution.

"Liposomes" refers to artificially prepared vesicles made of lipid bilayer, and having concentric phospholipid bilayers.

"Permeation enhancement" refers to an increase in the permeability of the skin or mucosal tissue to the selected active pharmaceutical ingredient.

"Scar" refers to a growth of collagen beneath the skin that is formed as the result of wound healing.

"Abnormal scar" refers to the over-expression of collagen in a scar, leaving an unaesthetic mark.

"Silicone" refers to polymeric organic silicone compounds obtained as oils.

"Topical administration" refers to delivery of a topical drug or active pharmaceutical ingredient to the skin or mucosa, providing a local effect.

"Transdermal drug delivery" refers to administration of a drug to the skin surface of an individual so that the drug passes through the skin tissue and into the individual's blood stream, therefore, providing a systemic effect.

"Transdermal pharmaceutical composition" refers to topical medications that may be used in different application form, such as, ointments, creams, lotions, pastes, gels, etc., and which releases one or more active drugs (e.g., dimenhydrinate) at a predetermined rate over a defined period of time to a defined site of application.

DESCRIPTION

The present disclosure relates to a synergistic mixture of a corticoid, such as betamethasone valerate, and an antialergic, such as tranilast, with a transdermal gel employed as a medication for scar treatment with increased skin permeability of active pharmaceutical ingredients (APIs). The disclosed formulations may be employed for reducing the scar formation, suppressing collagen production in scars including new scars, old scars, surgical scars, keloids, stretch marks, hypertrophic scars, or skin conditions that would benefit from barrier protection.

The nature of wound repair depends upon the tissues involved. An important aspect of wound healing is the rate at which a wound gains tensile strength. Skin exhibits tension and extensibility. Skin tension is one of the determining factors in the response to a wound and varies with age and site. Skin has multiple layers, including keratin, epidermis and dermis and includes cells, a fibrous network composed of collagen and elastin and an amorphous ground substance which consists of protein polysaccharides, glycoproteins, globular proteins, salts, and water. If only the epidermis is damaged, as in most minor injuries, keratinocytes migrate from the edge of the wound and eventually cover it, reforming the epidermis and keratin.

If all skin layers are damaged or destroyed, new connective tissue, called granulation tissue, must first fill the wound space. This tissue is formed by deposition of extracellular matrix components, for example, collagen, by fibroblasts which migrate into the wound space. The synthesis and deposition of collagen is an important event in wound healing and the rate of collagen synthesis varies in different organs.

Proper wound healing will result in an invisible scar. Early in the process, scars are red or dark and raised, but will become paler and flatter over time. It may take up to 24 months for a scar to develop and mature to its stable form and appearance.

Wound healing is commonly divided into four separate phases: coagulation, inflammation, migration and proliferation, and remodeling. Soon after a wound occurs in a subject, the wound healing process starts with a coagulation of fibrin and fibronectin to form a matrix or a clot and a gathering of platelets at the wound site. As the platelets coagulate, inflammatory cells, such as neutrophils, lymphocytes, and macrophages, are also attracted to the wound site and release factors for wound healing.

The final stage is involved in a remodeling process which changes the deposition pattern of matrix components. As described, the initial matrix is a clot of fibrin and fibronectin resulting from homeostasis. With the proliferation and migration of fibroblasts, collagen is synthesized and deposited replacing and rearranging the initial matrix with aid from proteases. Collagen fibers gradually increase in thickness and align along the stress line of the wound. At the end of a normal scar formation, the final scar shows collagen fibers mostly parallel to the epidermis.

Thus, the process is a delicately balanced equilibrium between growth and degradation. Any aberrations in the process may tip the balance toward a pathological abnormality in wound healing or an excessive deposit of scarring tissues. For example, an excessive deposition of scar tissues in skin during a wound healing process may result in, for example, keloids or hypertrophic scars. Keloids are a disorder in wound healing where excessive scar tissue proliferates beyond the boundary of the original wound. In contrast, hypertrophic scars occur when a trauma or injury to the deep dermis; however, the excessive deposition of scar tissue is confined to the margin of the original wound. In both cases, over accumulation or expression of collagen is believed to be the cause.

The excessive deposit or accumulation of collagen or an overexpression of collagen may be an elevated level of collagen at a wound site or in a scar which is higher than the normal level of collagen at a wound site undergoing a normal healing process or in a normally formed scar. The abnormal scars or the abnormalities in wound healing may include, but are not limited to, fibrosis, fibromatosis, keloidosis, adhesions (e.g. surgical adhesions), hypertrophic scars, fibrocystic conditions, and joint stiffness. Abnormal scars or abnormalities in wound healing may also be categorized into various conditions based on the type of tissue in which a wound occurs. Abnormal scar formation in skin may lead to, for example, keloid, hypertrophic scar, contracture, or scleroderma.

By inhibiting the excessive deposition of collagen, scar formation may be prevented and the wound healing process may be accelerated significantly.

According to an embodiment, the disclosed formulation may include a synergistic combination of active pharmaceutical ingredients (API) and a transdermal gel. Each of these components may bear significant healing properties, and employed together may be employed as treatment of scars. The components of the base may include silicone, pracaxi oil, seje oil, and the components of the API may include betamethasone valerate and tranilast. The combination of such components may exhibit enhanced healing properties, providing organic acids with antioxidant, antibacterial, and antifungal properties as well.

Active Pharmaceutical Ingredients (APIs)

Betamethasone Valerate

Betamethasone Valerate may be a potent topical corticosteroid. Topical corticosteroids have anti-inflammatory, antipruritic, and vasoconstrictive actions when administered topically. Therefore, betamethasone valerate may be generally used in inflammatory skin conditions, as betamethasone valerate may reduce inflammation and may help to relieve the symptoms of inflammatory, anti-inflammatory steroids skin problems, such as eczema, psoriasis, and dermatitis. Betamethasone valerate may be absorbed into the body even though is prescribed for skin problems. This may lead to side effects that affect parts of the body other than the skin. If betamethasone valerate is used for a long time, in large amounts or is covered with a dressing, these side effects are more likely to occur.

Betamethasone valerate may be obtained at various suppliers, such as LGM Pharma, Nashville, Tenn. and ALLICHEM LLC., Baltimore, Md., among others.

Tranilast

Tranilast has been known as a useful drug for treatments of asthma, atopic dermatitis, and allergic rhinitis. Several reports have shown that tranilast may prevent or act to improve keloid and hypertrophic scars. Tranilast decreases the weight of granulation and inhibits the collagen synthesis by human keloid tissues transplanted into the backs of mice and by carrageen in-induced granulation-tissues in rats. Tranilast specifically suppresses the collagen synthesis rather than the cell proliferation by cultured fibroblasts derived from human keloid tissues. In general, the inhibition of protein synthesis by corticosteroids has been considered the reason for decreased collagen synthesis in dermal tissue. It has also been suggested that tranilast may inhibit collagen synthesis of fibroblasts from keloid and hypertrophic scar tissue through suppressing the release of TGF-beta 1 (a mediator that stimulates collagen synthesis) from fibroblasts. Tranilast has also been shown to be useful in treating allergic conjunctivitis, atopic dermatitis, eczema, oligozoospermia, and otitis media. Tranilast is also known a mast cell stabilizer, inhibiting the release of chemical mediators such as histamine.

Other dermatological challenges may be effectively treated with tranilast. Using concentrations of between about 2% w/w to about 10% w/w in a vanishing cream base, such conditions as atopic dermatitis and eczema have been successfully treated. Tranilast also has been used in animals for the same conditions. There is evidence that patients with psoriasis can benefit from the use of topical tranilast. Through tranilast's antiangiogenesis and anti-inflammatory effects, the chemical mediators that cause the recurrent erythrematous skin plaques may be reduced.

The ophthalmic use of tranilast is well-documented. A solution of 0.5% w/w tranilast has been found useful in treating allergic conjunctivitis. There are also indications that the inhibition of collagen synthesis by tranilast may be useful in reducing scarring and pterygium formation in the eye after surgeries of the eye. The dose in all cases may be one drop in each eye four times a day. Tranilast even may have a place in treatment of mild cases of dry eye syndrome.

Studies have been conducted in children with otitis media with effusions and children with secretory otitis media. In the children with secretory otitis media, tranilast can reduce the number of glycoprotein fragments in the middle ear. These fragments cause the degranulation of mast cells and endothelial cells which can cause a local inflammatory response. The oral dose in these children was 5 gm/kg, and for adults, the oral dose may be about 300 mg per day in divided doses.

Studies also have been conducted in men with low sperm counts. An improvement in sperm count was seen in some patients. There also was an increase in the number of pregnancies in those studies. Tranilast also was studied alone and in combination with allopurinol for the treatment of gout. Oral daily doses of about 300 mg to about 900 mg of tranilast were used. These studies showed the uricosuric effects of tranilast as well as its anti-inflammatory activity. Headache was the most common side effect while a few cases of elevated liver enzymes were seen.

Tranilast is well-absorbed when taken orally but, because it is metabolized in the liver, periodic liver function tests should be done with long-term therapies.

Tranilast has many uses both orally and topically and it may be one of the most versatile agents available. Because of tranilast's usefulness in so many dermatological complaints, tranilast may be one of the first agents considered for keloids, hypertrophic scars, atopic dermatitis, and psoriasis.

Tranilast may be purchased from vendors, such as Kissei Pharmaceutical Co., Nagano, Japan, among others.

Transdermal Gel

Fatty acids, such as oleic acid, and lauric acid, among others, when used by themselves, may be irritating when applied to the skin, which makes them difficult to use as permeation enhancers. While having an irritating effect on the skin, these acids are also effective vehicles at delivering drugs through the skin.

According to an embodiment, betamethasone valerate and tranilast may be combined with a transdermal gel. The gel may have unique ingredients that may give to the disclosed formulation potential healing and soothing power, emolliency and mild penetration. Ingredients within the transdermal gel may include silicone, pracaxi oil and seje oil. While the transdermal gel is safe and effective, it may include natural ingredients that assist with penetration of betamethasone valerate and tranilast through the skin. Components present in the transdermal gel are oils that are rich sources of essential fatty acids, behenic acid, oleic acid, and in some instances, lauric acid.

Pracaxi Oil

Pracaxi oil is rich in organic acids with antioxidant, antibacterial and antifungal properties. Pracaxi oil may be obtained from the seed oil of *Pentaclethara Macroloba* tree. Pracaxi oil may include about 20% behenic acid and about 35% oleic acid. In some cases, it may include more than these percentages. As the behenic acid and oleic acid are present in the oil, the effects of the acids may be less irritating on the skin, and as such makes the oil a good choice for one of the ingredients of a penetration enhancer. This oil has been widely employed for its cosmetic, therapeutic, and medicinal properties. Scientific studies have shown that Pracaxi oil has strong antibacterial, antiviral, antiseptic, antifungal, antiparasitic, and anti-hemorrhagic properties. Pracaxi oil has been reported to also aid lighten hyper-pigmentation caused by hormonal changes, such as insect bites, abrasions, cuts, and acne, besides improving the appearance of stretch marks.

The oil may have a high amount of solid matter, not fatty acids, which makes it solidify in cooler temperatures. The solid matter has gentle moisturizers and high cellular renewal properties, includes Vitamin E and has essential fatty acids which make it a suitable oil for anti-aging products intended to address both prematurely aged and sensitive skins.

The fatty acid composition of Pracaxi oil is illustrated below in table 1.

TABLE 1

Fatty acid composition of Pracaxi oil.

| Fatty Acids | Carbon Atoms | Composition % |
|---|---|---|
| Lauric | 12:00 | 1.3000 |
| Myristic | 14:00 | 1.2100 |
| Palmitic | 16:00 | 2.0400 |
| Stearic | 18:00 | 2.1400 |
| Oleic | 18:10 | 44.3200 |
| Linoleic | 18:20 | 1.9600 |
| Linolenic | 18:30 | 2.3000 |
| Behenic | 22:00 | 19.6700 |
| Lignoceric | 24:00 | 14.8100 |

Seje Oil

Seje oil is extracted from the mesocarp of the patauá palm and generally appears as a greenish-yellow and transparent liquid, with little odor and taste, having the physical appearance and composition of fatty acids that are similar to olive oil (*Olea europaea*). It has high content of unsaturated fatty acids. Due to its high content of oleic acid, seje oil may be used as skin moisturizers. The dry mesocarp of patauá palm may include about 7.4% protein and possesses an excellent amino acid composition. Because of this, the protein of patauá is one of the most valuable found among plants and may be compared with the meat or milk from cattle. The most abundant sterols were Δ-5 avenosterol and β-sitosterol, with relative contents of about 35% and about 38%, respectively. The most abundant aliphatic alcohols were those with 7, 8 and 10 carbon atoms. Among tocopherols, α-tocopherol was predominant. Aldehydes, such as heptanal, octanal, and decanal were present in the volatile fraction along with terpenoid compounds.

The fatty acid composition of seje oil is illustrated below in table 2.

TABLE 2

Fatty acid composition of seje oil.

| Fatty Acids | Carbon Atoms | Composition % |
|---|---|---|
| Palmitic | 16:00 | 13.2 |
| Palmitoleic | 16:10 | — |
| Stearic | 18:00 | 3.6 |
| Oleic | 18:10 | 77.7 |
| Linoleic | 18:20 | 2.7 |
| Linolenic | 18:30 | 0.6 |
| Arachidic | 20:00 | 2 |
| Unsaturated | | 81.6 |

Phosphatidylcholine

Phosphatidylcholines are a class of phospholipids that incorporate choline as a headgroup. They are a major component of biological membranes and may be easily obtained from a variety of readily available sources, such as egg yolk or soy beans, from which they are mechanically or chemically extracted using hexane. They are also a member of the lecithin group of yellow-brownish fatty substances occurring in animal and plant tissues.

Phosphatidylcholine is a constituent of cell membranes. It has the primary role of providing a structural framework for the membrane and maintains the permeability barrier. Furthermore, phosphatidylcholine plays a role in membrane mediated cell signaling, and is the major component of lecithin. Lecithin includes a series of components other than phosphatidylcholine, such as phospholipids, and glycolipids, among others.

Because the body uses phosphatidylcholine to make a brain chemical called acetylcholine, there is some interest in using it for treating "brain-centered" conditions, such as memory loss, Alzheimer's disease, anxiety, manic-depressive disorders, and a movement disorder called tardive dyskinesia.

Phosphatidylcholine may also be used for treating hepatitis, eczema, gallbladder disease, circulation problems, high cholesterol, and premenstrual syndrome (PMS); for improving the effectiveness of kidney dialysis; for boosting the immune system; and for preventing aging.

Generally, phosphatidylcholine is injected under the skin (subcutaneously) for treating non-cancerous fatty tumors (lipomas), excess fat around the eyelids, and yellowish cholesterol deposits just under the surface of the skin (xanthelasmas).

Phosphatidylcholine injections are now often compounded in pharmacies. However, in the U.S., phosphatidylcholine, when compounded and used as an injection solution, is considered an unapproved drug rather than a dietary supplement. Moreover, when phosphatidylcholine is taken by mouth, it may sometimes cause excessive sweating, stomach upset, and diarrhea; and taken in injections may cause irritation, swelling, redness, itching, burning, bruising, and pain at the injection site.

Although, these side effects usually go away over a period of several days, the transdermal application of phosphatidylcholine may avoid the mentioned side effects.

Silicone

Silicone in gel treatments may work in the same way as silicone sheets. Silicone may be effective at softening and flattening scars.

Transdermal gel may include long chain silicone polymer (polysiloxanes), and silicone dioxide. Long chain silicone polymers cross link with silicone dioxide.

Silicone increases hydration of stratum corneum and therefore facilitates regulation of fibroblast production and reduction in collagen production resulting in softer and flatter scar.

Additionally, silicone within the transdermal gel may protect the scarred tissue from bacterial invasion and may prevent bacteria-induced excessive collagen production in the scar tissue.

Furthermore, the transdermal gel may modulate the expression of growth factors, fibroblast growth factor β (FGF β) and tumor growth factor β (TGF β). TGF β stimulates fibroblasts to synthesize collagen and fibronectin. FGF β normalizes the collagen synthesis in an abnormal scar and increases the level of collagenases which breaks down the excess collagen, therefore balance of fibrogenesis and fibrolysis is ultimately restored.

According to other embodiments, the transdermal gel may include one or more oils having essential fatty acids, behenic acid, and oleic acid, one or more skin lipids, and a butter having linoleic acid and linolenic acid.

In other embodiments, the transdermal gel may include organic solvents as transdermal penetration enhancers, such as caprylic/capric triglycerides (medium chain triglycerides), ethyl alcohol, ethoxy diglycol, dimethyl sulfoxide (DMSO), glycerin, isopropyl myristate, isopropyl palmitate, and propylene glycol, among others.

Betamethasone Valerate and Tranilast with a Transdermal Gel

In an embodiment, the present disclosure provides a transdermal formulation that may be employed potentially as scar prevention formulations. Scars types that may be treated with the disclosed formula may include new scars, old scars, surgical scars, keloids, hypertrophic scars, stretch marks or skin conditions that would benefit from barrier protection. The disclosed formula may mild penetration. Additionally, the disclosed formula may be employed to treat skin spots and may be useful for psoriasis and rosacea.

The disclosed formulation may include a synergistic combination of active pharmaceutical ingredients (APIs) and about 50% w/w of a transdermal gel. The API may include a combination of about 0.05% w/w to about 1% w/w of betamethasone valerate, being most suitable of about 0.1% w/w, and about 0.2% w/w to about 5% w/w of Tranilast, being most suitable of about 1% w/w. The transdermal gel may include about 0.5% w/w by weight to about 15% w/w of pracaxi oil, being most suitable about 1% w/w by weight to about 5% w/w; about 0.5% w/w to about 15% w/w of seje oil, being most suitable, about 1% w/w to about 5% w/w; about 0.1% w/w to about 5% w/w of phosphatidylcholine, being most suitable about 0.5% w/w to about 2% w/w; and about 10% w/w to about 95% w/w of silicone, being most suitable about 10% w/w to about 50% w/w.

According to other embodiments, the transdermal gel may include one or more oils having essential fatty acids, such as behenic acid and oleic acid; one or more skin lipids; and a butter having linoleic acid and linolenic acid.

In other embodiments, transdermal gel may include organic solvents as transdermal penetration enhancers, such as caprylic/capric triglycerides (medium chain triglycerides), ethyl alcohol, ethoxy diglycol, dimethyl sulfoxide (DMSO), glycerin, isopropyl myristate, isopropyl palmitate, and propylene glycol, among others.

In an embodiment, the use of the combination of pracaxi and seje oil will increase the skin permeability of tranilast and betamethasone valerate, passing the stratum corneum and reaching the target area, particularly, because of the oil's high concentrations of oleic, linolenic, linoleic acids and sterols, particularly beta-sitosterol and stigmasterol.

Ingredients within the transdermal gel, act synergistically to increase the skin permeation of water and oil soluble products. When the transdermal gel described here is prepared, liposomes may be formed from the fatty acids, including behenic acid and oleic acid that are present in one or more oils, and may be stabilized by the phospholipids in the transdermal gel.

Increasing the permeability of the disclosed formulation, the time of treatment may be significantly reduced, and thus, reducing the time of results of treatment to a period of about 2 weeks to about 1 month.

Compounding Procedure

Various methods may be used to produce disclosed transdermal scar treatment composition. In one embodiment, an electronic mortar and pestle may be employed to triturate the APIs together. Subsequently, the resulting powders may be wet to make a smooth paste and then transferred to an electronic mortar and pestle, and bring to the final weight with the transdermal gel. Afterwards, the resulting paste may be mixed in the electronic mortar and pestle for about 2 minutes on a medium velocity. Next, the resulting paste may be processed through an ointment mill twice to reduce the particle size of the API and to eliminate any grittiness of the final preparation. Finally, the resulting preparation may be mixed for about another minute on the electronic mortar and pestle on a low velocity.

Administration Route

One embodiment of the present disclosure may be directed to a formulation for preventing abnormal scar formation or treating abnormal scars by administering the disclosed formula to a subject transdermally, directly onto a scar site.

The amount of tranilast and betamethasone valerate which may be combined with the base to produce a single dosage form may vary depending upon the subject being treated and the particular mode of administration.

Formulations for the transdermal administration of the disclosed formula may include powders, sprays, ointments, pastes, creams, lotions, solutions, patches, being preferred administration by transdermal gel. Tranilast and betamethasone valerate may be mixed with the transdermal gel.

According to an embodiment, the disclosed formula may be transdermally administered directly into a scar, twice a day (between about 2 g to about 6 g) for about 10 weeks to about 14 weeks, expecting results to show from the third week after starting administration.

Testing

The efficacy of the transdermal gel in scar therapy treatment was evaluated by visual and instrumental methods in an eight-week, randomized, double-blind, and controlled pilot trial conducted on eleven adult Caucasian subject volunteers. The transdermal gel showed qualitative and quantitative improvements in the following scar attributes: scar length, scar color/pigment intensity, scar texture/smoothness/roughness, and overall appearance in both old scars and new scars.

Efficacy of Transdermal Gel in Scar Therapy Treatment: A Randomized, Double-Blind, and Controlled Pilot Trial.

The efficacy of the transdermal gel in scar therapy treatment was evaluated by visual and instrumental methods in an eight week, randomized, double-blind, and controlled pilot trial. The evaluations were conducted at week zero (baseline) and at week eight.

At week eight of application the mixture, the scars of all subject volunteers were evaluated by both visual and instrumental methods. No adverse reactions were reported, on or around scarring, by any of the subject volunteers.

Visual Analog Scale (VAS): According to the VAS assessment, 20% of test group volunteers showed an improvement in scar length, 40% in scar color intensity, and 80% in scar texture/smoothness. On average, scar length was reduced 2.5%, scar color intensity 20%, and scar smoothness was increased 24.08%.

Clarity™ Pro: According to this imaging system, 74.30% of test group volunteers showed an improvement in scar pigment intensity and 100% showed an improvement in scar texture/smoothness. On average, scar pigment intensity was reduced 17.56% whereas texture/smoothness was reduced 22.32%.

Figure 1A:
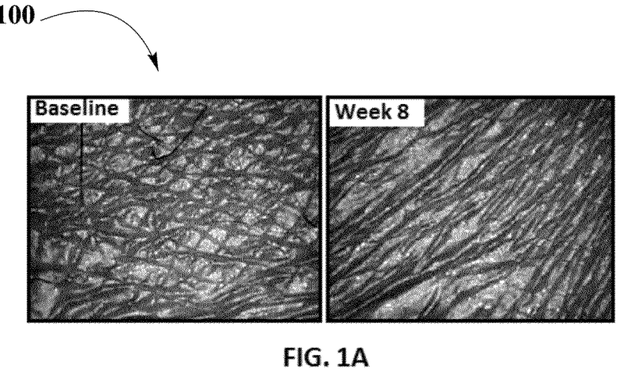
Figure 1B:
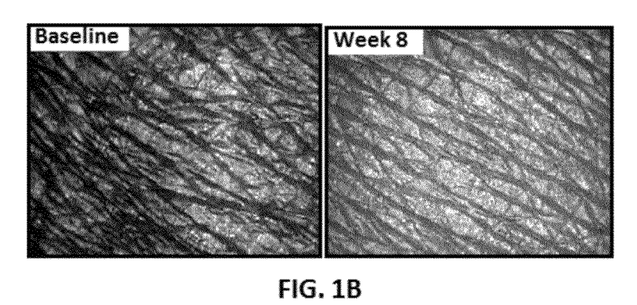

FIG. 1 illustrates the scar images 100 of two test group volunteers (A and B), displayed in FIG. 1 A and FIG. 1 B (respectively). Both figures show evident overall improvements in scar management. FIG. 1 A shows a subject's scar (A) before the application of the transdermal gel (left) and at week eight of the application of the transdermal gel (right). FIG. 1 B shows a subject's scar (B) before the application of the transdermal gel (left) and at week eight of the application of the transdermal gel (right).

Figure 2A:
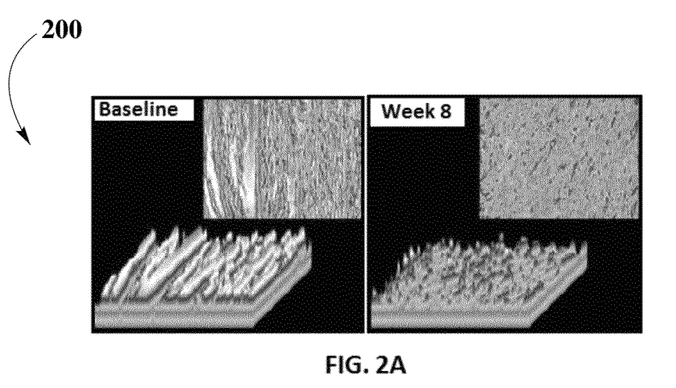
Figure 2B:
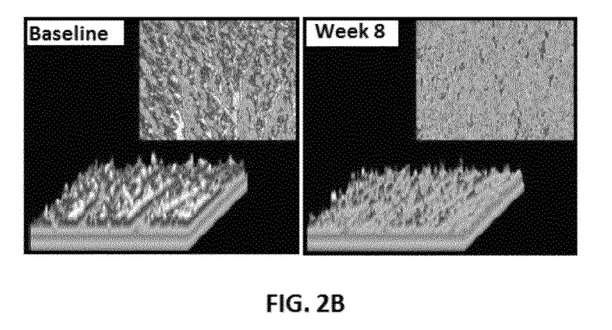

FIG. 2 depicts the skin contour replicas 200 of two test group volunteers (A and B), displayed in FIG. 2 A and FIG. 2 B (respectively). Both figures show evident overall improvements in scar texture/roughness. FIG. 2 A shows a subject's scar (A) before the application of the transdermal gel (left) and at week eight of the application of the transdermal gel (right). FIG. 2 B shows a subject's scar (B) before the application of the transdermal gel (left) and at week eight of the application of the transdermal gel (right).

According to this sampling technique, employing Replica™, 100% of test group volunteers showed an improvement in scar texture/roughness, which was reduced, on average, 16.01% (table 3).

TABLE 3

Percentage of test group subjects with improvement and average percentage of improvement in relation to scar texture/roughness.

| Scar | % subjects (with improvement) | % improvement (from baseline) |
|---|---|---|
| Texture/roughness | 100% | 16.01% |

As shown in the previous figures, the transdermal gel showed qualitative and quantitative improvements in the following scar attributes: scar length, scar color/pigment intensity, scar texture/smoothness/roughness, and overall appearance in both old scars and new scars. Thus, the transdermal gel may be recommended in scar therapy treatment, to be used alone or as a base for the incorporation of active substances.

Results from other cases showing the effectiveness of the transdermal gel may be described in the following figures.

Transdermal Gel for Treatment of Ankle Scars (Old & New)

The transdermal gel was applied on ankle scars (old & new) and an overall improvement of both ankle scars was observed in a very short period of time.

Figure 3A:
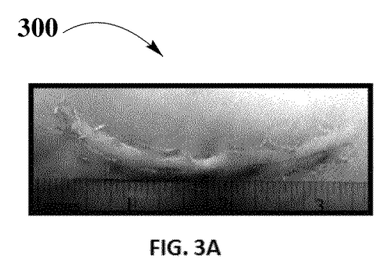
Figure 3B:
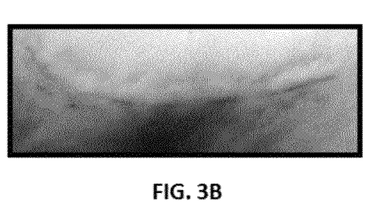

FIG. 3 shows the overall appearance of the patient's new scar 300, before (FIG. 3 A) and two weeks after (FIG. 3 B) the application of the transdermal gel. The patient was a 50-year-old woman diagnosed with osteochondritis dissecans of the right talus who went in for osteochondral allograft surgery, for the second time, in March 2013. The patient was advised to wait 10 days, following the removal of the stitches, before applying any topical scar treatments. After this period, the patient initiated treatment with (only) the transdermal gel twice daily for two weeks, lightly massaging into and around the scar area.

The patient reported that, after this treatment, the scar was very smooth and it had reduced in size over time. At the end of two weeks, the scar was considerably flattened and wearing a sock did not irritate the area.

The study was also performed on a type 1 diabetic 57-year-old woman, whom fractured her ankle during a ski accident in March 2009. The patient underwent three reconstructive surgeries between 2009 and 2012, which resulted in three ankle scars. After the application of different products, the patient was still unsatisfied with the resulting unaesthetic scars. In April 2013, it was suggested the patient apply the transdermal gel twice daily on the old scars.

The patient reported that in only one week had significant improvements in the overall appearance of the scars. The thickness almost completely disappeared, the dark color faded, and the skin softened.

Figure 4A:
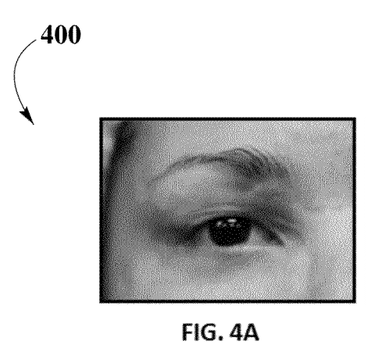
Figure 4B:
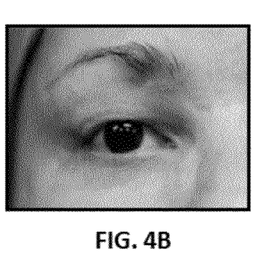

FIG. 4 shows patient's facial scars 400. FIG. 4 A shows patient's facial scars 400 before applying the transdermal gel and FIG. 4 B shows patient's facial scars 400 after applying the transdermal gel.

The following examples are intended to illustrate the scope of the disclosure. It is to be understood that other procedures known to those skilled in the art may alternatively be used.

EXAMPLES

Example #1 is a test of a transdermal gel for facial scars (shown in FIG. 4), where a compounded medicine including the transdermal gel was applied on facial scars (old) and an overall improvement of the facial complexion was observed following only 3 weeks.

The study was performed on a 22-year-old female that was severely scarred on the face during a car accident in October 2009. After six plastic surgeries and the application of different products, the patient was still unsatisfied with her complexion. In March 2013, a compounded medicine including pentoxifylline 1%, caffeine 1%, tranilast 1%, and the transdermal gel was suggested to be applied twice a day on the (old) facial scars.

As seen in FIG. 4 B, after 3 weeks of treatment, the patient experienced softening of her skin and overall improvement of her complexion.

The patient reported to have tried many products with little satisfaction, but the transdermal gel showed improved results in a very short amount of time. The transdermal gel reduced the redness of the scars and gave the skin a more uniform look and texture.

Example #2 is an embodiment of the disclosed formulation, where active pharmaceutical ingredients (API) added to the base may be betamethasone valerate 0.1% w/w/Tranilast 1% w/w; which may be useful for an inflamed scar. For a more aggressive approach, the tranilast may be increased up to a concentration of 10% w/w.

Example #3 is an embodiment of the disclosed formulation, where API added to the base may be collagenase 350 U/Gm/Hyaluronidase 250 U/Gm.

Example #4 is an embodiment of the disclosed formulation, where API added to the transdermal gel may be tamoxifen citrate 0.1% w/w/tranilast 1% w/w/caffeine citrated 0.1% w/w/lipoic acid 0.5% w/w. This embodiment combines a proven agent against scars, tamoxifen, with tranilast. This formula may be useful in vigorous keloids or scars.

Example #5 is an embodiment of the disclosed formulation, where API added to the transdermal gel may be EGCg 1% w/w/dimethyl sulfone 2% w/w/tranilast 1% w/w/ascorbic acid 2% w/w. This embodiment combines the antioxidant activity of green tea and the anti-inflammatory action of dimethyl sulfone (also known as MSM) with tranilast. This embodiment may be a basic formula for keloids and hypertrophic scars.

Example #6 is an embodiment of disclosed formulation, where API added to the transdermal gel may be EGCg 1% w/w/dimethyl sulfone 5% w/w/ascorbic acid 2% w/w/caffeine 1% w/w.

Example #7 is an embodiment of the disclosed formulation, where API added to the transdermal gel may be tranilast 1% w/w/pentoxifyllin (0.2% w/w-5% w/w).

While various aspects and embodiments have been disclosed here, other aspects and embodiments may be contemplated. The various aspects and embodiments disclosed here are for purposes of illustration and are not intended to be limiting, with the true scope and spirit being indicated by the following claims.

What is claimed is:

1. A formulation for inhibiting scar formation comprising:
   a) betamethasone valerate;
   b) tranilast; and
   c) a transdermal gel comprising about 10% w/w to about 95% w/w silicone; about 0.5% w/w to about 15% w/w pracaxi oil; about 0.5% w/w to about 15% w/w seje oil; and about 0.1% w/w to about 5% w/w phosphatidyl choline.

2. The formulation of claim 1, wherein the betamethasone valerate is about 0.05% w/w to about 1% w/w.

3. The formulation of claim 1, wherein the tranilast is about 0.2% w/w to about 5% w/w.

4. The formulation of claim 1, wherein the transdermal gel is about 50% w/w.

5. The formulation of claim 1, wherein the pracaxi oil is about 1% w/w to about 5% w/w and the seje oil is about 1% w/w to about 5% w/w.

6. The formulation of claim 1 further comprising a transdermal penetration enhancer.

7. The formulation of claim 6, wherein the transdermal penetration enhancer comprises caprylic/capric triglycerides, ethyl alcohol, ethoxy diglycol, dimethyl sulfoxide, glycerin, isopropyl myristate, isopropyl palmitate, or propylene glycol.

8. The formulation of claim 1, wherein the transdermal gel comprises about 10% w/w to about 50% w/w silicone; about 0.5% w/w to about 10% w/w pracaxi oil; about 0.5% w/w to about 10% w/w seje oil; and about 0.5% w/w to about 2% w/w phosphatidyl choline.

9. The formulation of claim 8, wherein the transdermal gel comprises about 1% w/w to about 5% w/w pracaxi oil; about 1% w/w to about 5% w/w seje oil; about 0.5% w/w to about 2% w/w phosphatidyl choline; and about 10% w/w to about 50% w/w silicone.

10. The formulation of claim 8, wherein the betamethasone valerate is about 0.05% w/w to about 1% w/w and wherein the tranilast is about 0.2% w/w to about 5% w/w.

11. The formulation of claim 1 further comprising collagenase.

12. The formulation of claim 1 further comprising hyaluronidase.

13. The formulation of claim 1, wherein the transdermal gel comprises about 0.5% w/w to about 2% w/w phosphatidyl choline.

14. The formulation of claim 1, wherein the pracaxi oil is about 0.5% w/w to about 5% w/w.

15. The formulation of claim 1, wherein the seje oil is about 0.5% w/w to about 5% w/w.

16. A formulation comprising
   a) about 0.1% w/w betamethasone valerate;
   b) about 1% w/w tranilast; and
   c) a transdermal gel comprising i) about 1% w/w to about 5% w/w pracaxi oil; ii) about 0.5% w/w to about 15% w/w seje oil; iii) about 0.5% w/w to about 2% w/w phosphatidyl choline; and iv) about 10% w/w to about 50% w/w silicone.

17. The formulation of claim 16 further comprising a transdermal penetration enhancer.

18. The formulation of claim 16, wherein the transdermal gel comprises about i) 1% w/w to about 5% w/w pracaxi oil; ii) about 1% w/w to about 5% w/w seje oil; iii) about 0.5% w/w to about 2% w/w phosphatidyl choline; and iv) about 10% w/w to about 50% w/w silicone.

19. The formulation of claim 18 further comprising collagenase.

20. The formulation of claim 18 further comprising hyaluronidase.

\* \* \* \* \*